(12) United States Patent
Lee et al.

(10) Patent No.: US 10,646,664 B2
(45) Date of Patent: May 12, 2020

(54) BODY CONTOUR ADAPTABLE AUTOINJECTOR DEVICE

(71) Applicant: Amgen Inc., Thousand Oaks, CA (US)

(72) Inventors: Mark Ka Lai Lee, Newbury Park, CA (US); Stephanie Toy, Moorpark, CA (US); Valerie M. Fenster, Woodland Hills, CA (US)

(73) Assignee: AMGEN INC., Thousand Oaks, CA (US)

( * ) Notice: Subject to any disclaimer, the term of this patent is extended or adjusted under 35 U.S.C. 154(b) by 434 days.

(21) Appl. No.: 14/776,693

(22) PCT Filed: Mar. 14, 2014

(86) PCT No.: PCT/US2014/027874
§ 371 (c)(1),
(2) Date: Sep. 14, 2015

(87) PCT Pub. No.: WO2014/143770
PCT Pub. Date: Sep. 18, 2014

(65) Prior Publication Data
US 2016/0038689 A1 Feb. 11, 2016

Related U.S. Application Data

(60) Provisional application No. 61/792,744, filed on Mar. 15, 2013.

(51) Int. Cl.
*A61M 5/32* (2006.01)
*A61M 5/20* (2006.01)
(Continued)

(52) U.S. Cl.
CPC ............ *A61M 5/3287* (2013.01); *A61M 5/19* (2013.01); *A61M 5/20* (2013.01); *A61M 5/2033* (2013.01);
(Continued)

(58) Field of Classification Search
CPC .. A61M 5/14248; A61M 5/3287; A61M 5/19; A61M 5/20; A61M 5/2033;
(Continued)

(56) References Cited

U.S. PATENT DOCUMENTS 5,411,485 A * 5/1995 Tennican ............ A61M 5/1408
600/432
6,312,412 B1 11/2001 Saied et al.
(Continued)

FOREIGN PATENT DOCUMENTS

CN 102123753 A 7/2011
JP 2002-505601 A 2/2002
(Continued)

OTHER PUBLICATIONS

Chinese Patent Application No. 201480021632.4, Notification of the First Office Action, dated Apr. 10, 2018.
(Continued)

*Primary Examiner* — Amber R Stiles
*Assistant Examiner* — Tezita Z Watts
(74) *Attorney, Agent, or Firm* — Marshall, Gerstein & Borun LLP

(57) ABSTRACT

An injector for delivering a therapeutic product may include a base having a flexible surface that conforms to various body contours of a patient and defines one or more an injection chambers. The injector may have a height that is substantially less than its width, thereby defining a low profile, which provides a larger more stable base that can pinch or stretch the skin in a controlled manner. The larger base can also accommodate larger volumes via multiple injection chambers and/or large combined primary containers.

20 Claims, 7 Drawing Sheets

(51) Int. Cl.
*A61M 5/19* (2006.01)
*A61M 5/42* (2006.01)
*A61M 5/315* (2006.01)
*A61M 5/44* (2006.01)
A61M 5/30 (2006.01)
A61M 5/34 (2006.01)

(52) U.S. Cl.
CPC ...... *A61M 5/31576* (2013.01); *A61M 5/3202* (2013.01); *A61M 5/425* (2013.01); *A61M 5/44* (2013.01); A61M 5/2053 (2013.01); A61M 5/326 (2013.01); A61M 5/445 (2013.01); A61M 2005/206 (2013.01); A61M 2005/3022 (2013.01); A61M 2005/341 (2013.01)

(58) Field of Classification Search
CPC ............ A61M 5/31576; A61M 5/3202; A61M 5/425; A61M 5/44; A61M 5/2053; A61M 5/326; A61M 5/445; A61M 2005/206; A61M 2005/3022; A61M 2005/341
USPC ........................................................ 604/174
See application file for complete search history.

(56) References Cited

U.S. PATENT DOCUMENTS

| | | | |
|---|---|---|---|
| 7,780,636 B2* | 8/2010 | Radmer | A61M 5/14248 604/171 |
| 8,382,703 B1 | 2/2013 | Abdelaal | |
| 2002/0010423 A1 | 1/2002 | Gross et al. | |
| 2002/0123740 A1* | 9/2002 | Flaherty | A61M 5/14248 604/890.1 |
| 2003/0171716 A1* | 9/2003 | Ejlersen | A61M 5/46 604/117 |
| 2004/0115068 A1* | 6/2004 | Hansen | A61M 5/14224 417/379 |
| 2004/0147901 A1 | 7/2004 | Py et al. | |
| 2006/0200083 A1 | 9/2006 | Freyman et al. | |
| 2006/0264926 A1* | 11/2006 | Kochamba | A61M 5/14248 606/41 |
| 2007/0156096 A1* | 7/2007 | Sonoda | A61M 37/00 604/174 |
| 2009/0028824 A1 | 1/2009 | Chiang et al. | |
| 2011/0021998 A1 | 1/2011 | Dikeman et al. | |
| 2011/0046454 A1* | 2/2011 | Ejlersen | A61B 5/6848 600/309 |
| 2011/0144584 A1 | 6/2011 | Wozencroft | |
| 2011/0166512 A1* | 7/2011 | Both | A61M 5/14248 604/67 |
| 2011/0306929 A1* | 12/2011 | Levesque | A61M 5/158 604/150 |
| 2012/0289905 A1 | 11/2012 | Julian et al. | |

FOREIGN PATENT DOCUMENTS

| | | |
|---|---|---|
| JP | 2005518253 A | 6/2005 |
| WO | 1994023777 A1 | 10/1994 |
| WO | WO-98/57683 A1 | 12/1998 |
| WO | WO-03/072172 A2 | 9/2003 |
| WO | 2009015389 A2 | 1/2009 |
| WO | WO-2010/018411 A1 | 2/2010 |
| WO | 2012145752 A2 | 10/2012 |
| WO | WO-2012145752 A2 | 10/2012 |

OTHER PUBLICATIONS

Japanese Patent Application No. 2016-502651, Notice of Reasons for Rejection, dated Sep. 3, 2018.
First Examination Report for Australian Application No. 2014228177 dated Nov. 9, 2017.
Chinese Patent Application No. 201480021632.4, Notification of the Fourth Office Action, dated Oct. 8, 2019.
Israeli Patent Application No. 241030, Office Action, dated Apr. 7, 2019.
"Extended European Search Report" issued in counterpart European Patent Application No. 14762224.5 dated Oct. 11, 2016.
"Office Action" issued in counterpart Taiwan Patent Application No. 103109330 dated Aug. 15, 2016.
"International Search Report and Written Opinion", Issued in counterpart International Application No. PCT/US2014/027874, dated Aug. 8, 2014.

* cited by examiner

BODY CONTOUR ADAPTABLE AUTOINJECTOR DEVICE

FIELD

The disclosure relates to autoinjector devices. More particularly, the disclosure relates to an autoinjector device having a low profile, body contour adaptable construction and configuration.

BACKGROUND

Current autoinjector (AI) devices are held against the body while an injection needle pierces the skin to administer a pharmaceutical product or drug. The drug product or drug can comprise a monoclonal antibody or other protein. To operate the AI device, the user grips the device and applies a downward force against the skin that activates or arms the AI device. The user then presses a button with a finger or thumb to cause the needle to be deployed and the injection cycle to begin e.g. the syringe stopper/plunger arrangement moves the drug downward into the skin at the injection site.

During needle insertion and stopper/plunger movement, the interface/surface area between the user's skin and the AI device's physical area touching the skin (and encompassing the needle) should remain in place to avoid device and/or needle slippage or movement on the surface of the skin. This occurs to enable a full drug dose delivery, to avoid drug leakage on the skin's surface, and/or, to avoid user injury from a bent or broken needle during the injection process. Additionally, for user comfort, it is advised that the injection site's skin area, and directly under the AI, be kept taut to facilitate the injection procedure.

Most AI devices have a vertical or pen-like construction/profile, which does not provide a natural contour form that accommodates the shape of the human palm/hand/fingers. In addition, the vertical-elongated construction/profile of AI pen devices makes them difficult to hold stable against the body during an injection because the physical surface area of the device that contacts the skin is relatively small, which results in a concentration of compression forces and user discomfort. Consequently, device and/or needle slippage or movement often occurs, which can cause drug leakage on the skin's surface, and user injury from a bent or broken needle during the injection process. Further, the use of AI pen devices can be a significant challenge for seniors or finger function compromised users (e.g., patients with arthritis) and consequently, treatment can be hindered.

Accordingly, an improved AI device is needed which avoids the problems associated with conventional AI pen devices.

SUMMARY

An injector for delivering a therapeutic product may comprise, in some embodiments, a base having a flexible surface that conforms to various body contours of a patient, the surface defining an injection chamber therein.

Some embodiments of the injector may further comprise a cover disposed over the base.

In some embodiments of the injector, the surface may comprise a flexible layer for forming a vacuum between the flexible layer and the skin of the patient.

In some embodiments of the injector, the flexible layer stretches or pinches the skin.

Some embodiments of the injector may further comprise a flexible isolator disposed over the injection chamber, the isolator for drawing a portion of the skin up into the injection chamber defined in the surface.

In some embodiments of the injector, the isolator may have a concave surface for drawing the portion of the skin up into the injection chamber defined in the surface.

Some embodiments of the injector may further comprise a syringe disposed within the injector and containing a therapeutic product, a needle shield removably attached to the syringe, and a peelable substrate disposed over the surface for removing the needle shield from the syringe.

In some embodiments of the injector, the peelable substrate may have a structure which can be folded into a pull-tab to facilitate removal of the peelable substrate from the surface of the base.

In some embodiments of the injector, the peelable substrate may have a structure with opposing portions that can be folded down against one another to facilitate removal of the peelable substrate from the surface of the base.

In some embodiments of the injector, the peelable substrate may have a projection extending from an attachment surface thereof for attaching the peelable substrate to the needle shield.

In some embodiments of the injector, the cover may have a palm-button for pressing the cover toward the base to start an injection cycle of the injector.

In some embodiments of the injector, the cover may have at least one finger-pad for gripping the injector.

In some embodiments of the injector, the at least one finger-pad may be located on the cover to meet a gripping requirement of a certain patient population.

In some embodiments of the injector, the cover may be coated with a layer of material for hand or finger gripping of the injector.

In some embodiments of the injector, the cover may have a window for viewing the syringe during an injection cycle of the injector.

In some embodiments of the injector, the cover may have a window and mirror configuration for viewing the drug.

In some embodiments of the injector, the injector may have a low profile.

In some embodiments of the injector, the base may have a vent aperture, wherein movement of the cover relative to the base causes air to move through the vent aperture for releasing the vacuum generated between the flexible layer of the base and the skin.

In some embodiments of the injector, the syringe may have a needle for injecting the therapeutic product contained within the syringe into the patient and further comprising a carrier provided on the base, the carrier for moving the syringe between first and second positions during an injection cycle of the injector, the needle disposed within the injector in the first position, the needle extending from the base in the second position.

In some embodiments of the injector, the syringe may have a plunger for dispensing the therapeutic product from the syringe and through the needle and further comprising a plunger drive for driving the plunger through the syringe to dispense the therapeutic product from the syringe and through the needle, the plunger drive having one of a motor drive element, a spring drive element, a hydraulic drive element, or any combination thereof.

In some embodiments of the injector, the plunger drive may be activated by pressing a button feature on the cover.

In some embodiments of the injector, the plunger drive may be activated by pressing the cover toward the base.

Some embodiments of the injector may further comprise a carrier drive for moving the carrier between the first and second positions, the carrier drive having one of a motor drive element, a spring drive element, a hydraulic drive element, of any combination thereof.

In some embodiments of the injector, the carrier drive may be activated by pressing a button feature on the cover.

In some embodiments of the injector, the carrier drive may be activated by pressing the cover toward the base.

In some embodiments of the injector, the carrier drive may be disposed at an acute angle relative to the base.

Some embodiments of the injector may further comprise a needle guide for bending the needle into the injection chamber.

Some embodiments of the injector may further comprise a heating element disposed adjacent to the carrier for heating the therapeutic product contained in the syringe.

In some embodiments of the injector, the heating element may comprise an exothermic heating element.

In some embodiments, the injector may further comprise an indicator to communicate that the injector and therapeutic product are at the optimal operating condition.

In some embodiments of the injector, the syringe may have a plunger for dispensing the therapeutic product from the syringe and through the needle and may further comprise a plunger drive for driving the plunger through the syringe to dispense the therapeutic product from the syringe and through the needle and a carrier drive for moving the carrier between the first and second positions, each of the plunger and carrier drives having one of a motor drive element, a spring drive element, a hydraulic drive element, and or combination thereof.

In some embodiments of the injector, at least one of the plunger and carrier drives may be activated by pressing the cover toward the base or by pressing a button feature on the cover.

In some embodiments of the injector, the syringe may comprise at least two barrels coupled to the needle, each barrel containing a therapeutic product.

Some embodiments of the injector may further comprise at least a second carrier.

Some embodiments of the injector may further comprise at least a second syringe, the second carrier for moving the second syringe between the first and second positions.

Some embodiments of the injector may further comprise a container or syringe containing a therapeutic product.

In some embodiments, a method is provided comprising administering to a patient in need thereof a therapeutic product from a container in the injector.

DETAILED DESCRIPTION

It should be noted that while an autoinjector (AI) device is referred to throughout the disclosure, in some instances the device can also be referred to as an injector.

The autoinjector (AI) device of the disclosure may be constructed and adapted to have a height that is substantially less than its width, thereby defining a low profile, which provides a larger more stable base that can pinch or stretch the skin in a controlled manner. Accordingly, the AI device can easily maintain a skin/device interface thereby providing controlled injection depth and drug delivery. The larger base can also accommodate larger volumes via multiple injection chambers (site within the base where injection is carried out) and/or large primary containers and/or primary containers that are combined to one another. The primary container can comprise, inter alia, prefilled syringes or vials. In some embodiments of the AI device, injection chambers are arranged to facilitate an active anchoring system which alleviates the need to maintain a constant force on the AI device. Further, in some embodiments, activation of needle deployment, drug delivery, and needle withdrawal (injection cycle) may be accomplished using the palm of the hand thereby allowing greater ease of use than existing autoinjectors and accommodating a broader user population especially for dexterity challenged users.

Figure 1:
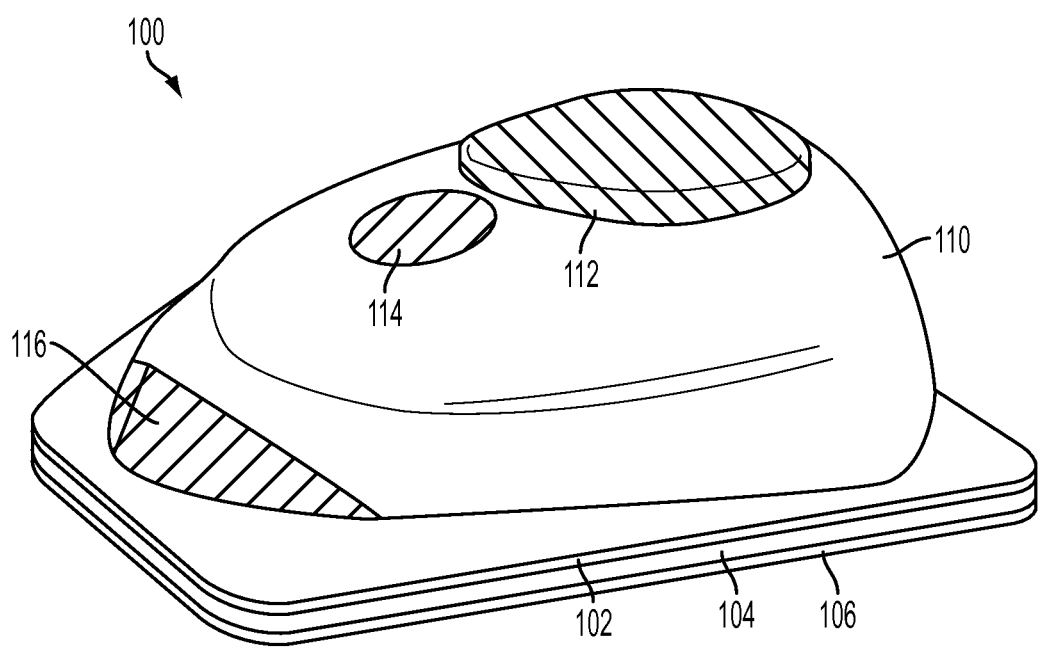
FIG. 1 is a perspective view of an embodiment of an AI device.

FIG. 1 is a perspective view of an embodiment of an AI device 100. The AI device 100 may include a base 102, a flexible layer 104, a releasable substrate 106, a cover 110, a palm-button 112, one or more finger-pads 114, and one or more drug container viewing windows 116. The base 102 may be constructed out of an impact resistant, rigid material, such as polycarbonate, acrylonitrile butadiene styrene (abs), or any other suitable material known to one of ordinary skill in the art.

Figure 2:
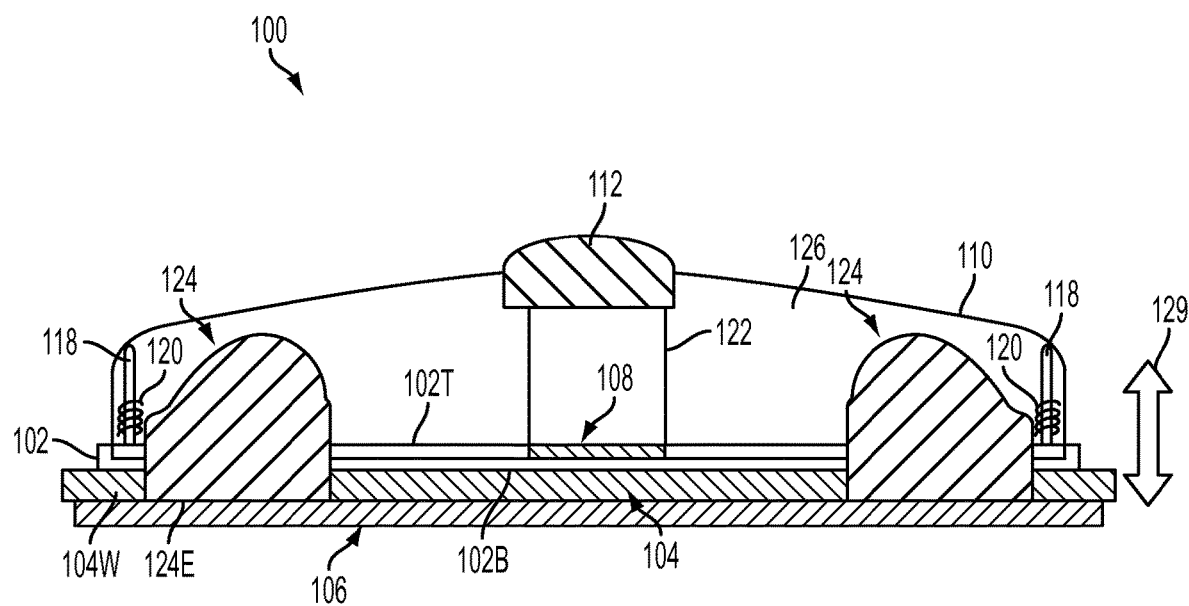
FIG. 2 is a sectional side view of the AI device of FIG. 1

FIG. 2 is a sectional side view of the AI device 100 of FIG. 1. As shown, the base 102 may be a planar member having top and bottom surfaces. The base 102 may have a substantially larger surface area than conventional "pen-style" autoinjectors thereby providing a more stable body interface. In various embodiments, the base 102 may have a diameter of 5 cm to 15 cm. The bottom surface 102B of the base 102 may be covered by the flexible layer 104, which may extend beyond the perimeter of the base 102. When the user presses the AI device 100 against the body, the flexible layer 104 allows the base 102 of the AI to conform to various contours of the user's body while either elevating (pinching) or depressing (stretching) the user's skin in a controlled manner, thereby forming a seal and vacuum between the base 102 and the skin of the user. The flexible layer 104 may be made of a bio-compatible (non-latex) material such as polyurethane, silicone-polyurethane co-polymer, hydro-gel, or any other suitable bio-compatible material capable of flexing that is known to one of ordinary skill in the art. In some embodiments, the flexible layer 104 may define a concave skin-contact surface. The flexible layer 104 may be covered with the releasable substrate 106 that may be peeled off from the flexible layer 104 of the base 102 when the patient is ready to use the AI device 100.

Figure 3:
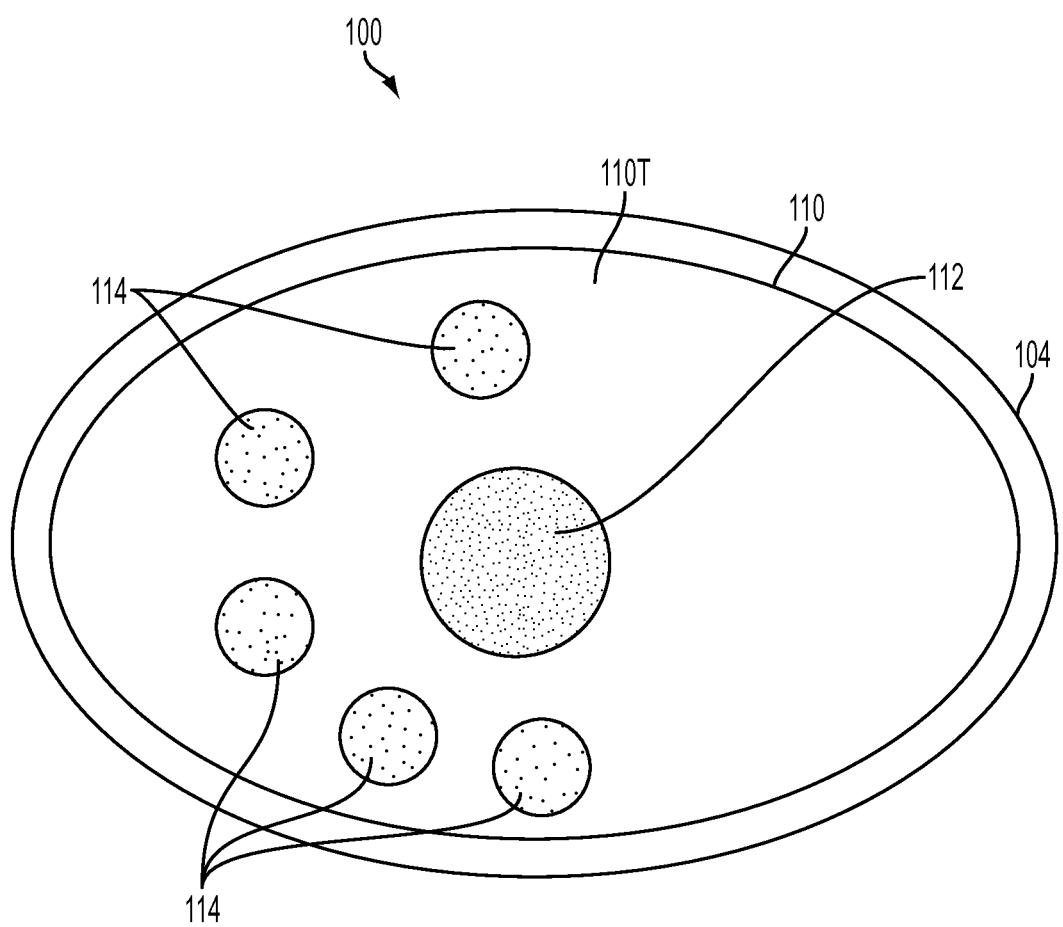
FIG. 3 is a top view of the AI device of FIG. 1.

Referring to FIG. 2 and also to FIG. 3, which is a top view of the AI device 100, the cover 110 may have an ergonomic oval, dome-shape configuration which allows the injector to be easily gripped and/or handled, thereby allowing the AI device 100 to operated by a broader range of users. The cover 110 may be constructed out of an impact resistance rigid material such as polycarbonate, abs or any other suitable material known to one of ordinary skill in the art. It should be understood that the configuration is not limited to being dome-shaped and any shape that provides an appropriate ergonomic effect can be used, provided that it meets other criteria described herein. The palm-button 112 may be integrated into the apex A or any other region of the cover 110 and aids the user in pressing the cover 110 down toward the base 102 with the user's palm to start an injection cycle of the AI device 100. The palm button 112 may be constructed out of a impact resistance rigid material, such as polycarbonate, abs, or any other suitable material known to one of ordinary skill in the art, and in some embodiments, may be coated with a bio-compatible (e.g. non-latex) material such as polyurethane, silicone-polyurethane co-polymer, or hydro-gel. Of course, other suitable materials known to one of skill in the art may also be used. In some embodiments, the palm-button 112 may extend entirely through the apex of the cover 110 so that it can coact with other components disposed within the AI device 100. In other embodiments, the palm-button 112 may only be integrated into a top surface 110T of the cover 110, at the apex thereof. In still further embodiments, the palm-button 112 may be integrated into the cover or top surface 110T thereof, in a location slightly offset from the apex.

Referring still to FIG. 3, the one or more finger-pads 114 may be integrated into the cover's top surface 110T at certain locations. The one or more finger-pads 114 allow the user to easily grip and/or handle the AI device 100 and may be constructed from a bio-compatible (non-latex) material such as polyurethane, silicone-polyurethane co-polymer, or hydro-gel. In some embodiments, the one or more finger-pads 114 may have a textured surface. The number of finger-pads 114 and their location on the cover 110 may be selected to meet a gripping requirement of a desired user population. For example, in some embodiments, the number and location of the finger-pads 114 may be selected to meet the gripping requirement of a user population having limited right-hand dexterity. In other embodiments, the number and location of the finger-pads 114 may be selected to meet the gripping requirement of a user population having limited left-hand dexterity. In still further embodiments, the number and location of the finger-pads 114 may be selected to meet the gripping requirement of a user population having limited left- and right-hand dexterity.

In alternate embodiments of the AI device, the palm and one or more finger gripping pads may be replaced with a layer of material (not shown), which covers entire the top surface of the cover 110 and facilitates hand or finger gripping of the AI device 100.

Referring again to FIG. 1, the one or more drug container viewing windows 116 may be formed in the cover 110. Each of the viewing windows allows the user to view a corresponding syringe or the drug contained therein, disposed within the AI device 100 or the level of drug within a syringe. In various other embodiments, the cover may have a window and mirror configuration for viewing the drug.

Figure 5:
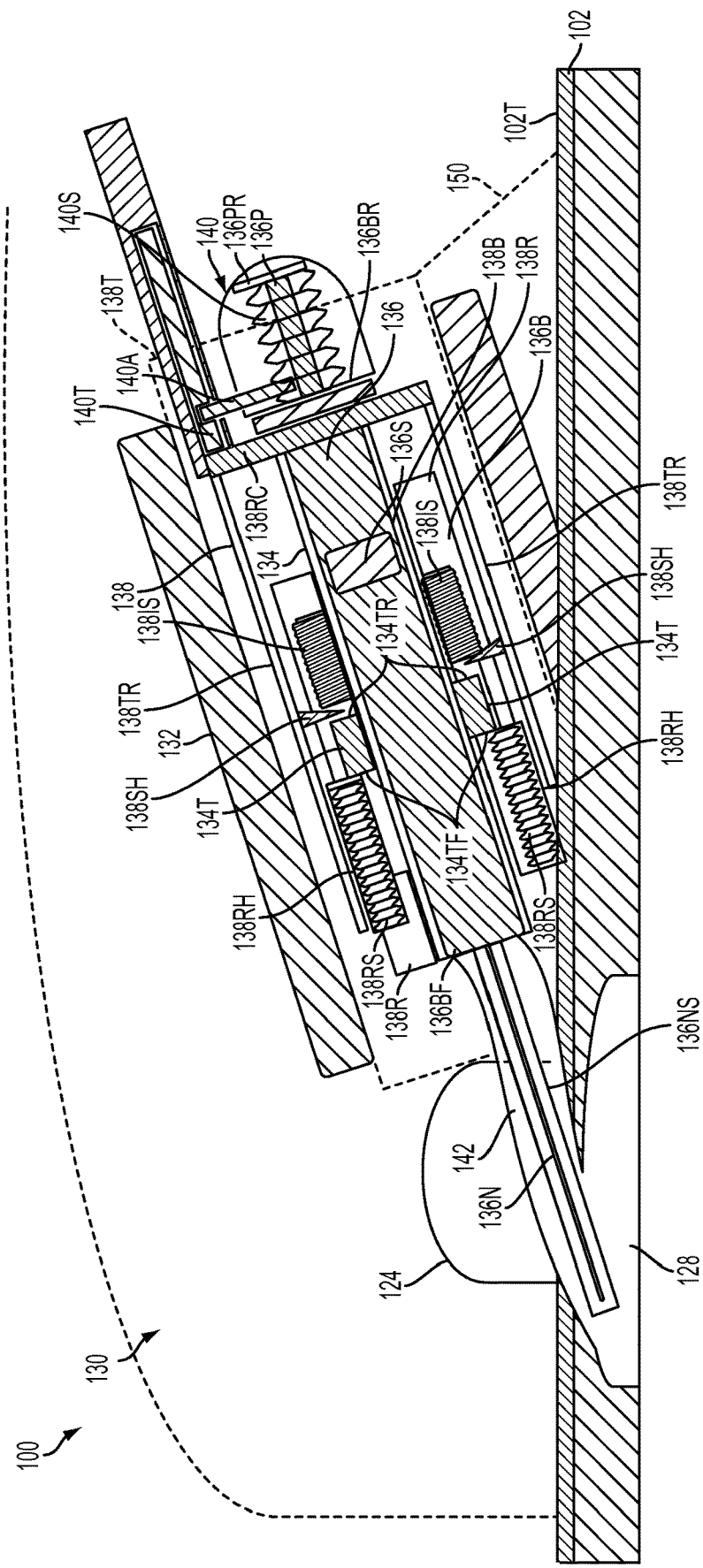
FIG. 5 is an enlarged sectional side view of an injection unit assembly shown in FIG. 4.

Referring again to FIG. 2, the AI device 100 may further include one or more injection site isolators 124, an air vent arrangement 108, a palm-button support post 122, and one or more collapsible cover return posts 118 and corresponding return springs 120, disposed within an interior 126 of the device 100. The isolators 124 may be made from a rigid material, such as poly-carbonate or abs plastic and further coated with a bio-compatible (non-latex) material, such as polyurethane, silicone-polyurethane co-polymer, hydro-gel, or any other suitable material known to one of ordinary skill in the art, to enable greater traction or grip. The injection site isolators 124 may extend through coaxial-aligned openings (not visible) in the base 102 and the flexible layer 104. Some embodiments of the injection site isolator 124 may have a dome-like structure with a bottom edge 124E that lies generally flush with the working surface 104W (the surface applied to the user's skin) of the flexible layer 104. The dome-like structure of the isolator 124 defines a space, which space forms an injection chamber 128 (FIG. 5). When the user presses the AI device 100 against his or her body, the isolator 124 pulls the skin located immediately below the isolator 124, up into injection chamber 128 defined therein.

Referring still to FIG. 2, upon application of the injector 100 to the skin the air vent arrangement 108 is initially open to displace air. Once a pocket of air has been displaced, the vent arrangement 108 closes, as the cover 110 and the base 102 float or move with respect to each other. After injection, the spring back of the cover 110 relative to the base 102, reopens the vent arrangement 108 for air to rush in and release the vacuum. The suction/suction release functions of the vent arrangement 108 (which activates suction (vacuum) and venting for suction release) may be activated in some embodiments, as the cover 110 moves in the appropriate direction relative to the base 102, as indicated by arrow 129. The air vent arrangement 108, in some embodiments, may include a vent aperture (not visible) that extends through the base 102 and a closure (not visible) to block/close and unblock/open the vent aperture when the cover 110 moves relative to the base 102. When the vent aperture is open, air that may be disposed within the palm-button support post 122 of the AI device 100 or air trapped between the skin and the flexible layer 104, can pass therethrough, depending upon whether the AI device 100 is in a suction mode or a suction release mode. The collapsible cover return post 118 may conventionally comprise two or more telescoping elements operatively connected to the return spring 120, which may be a coil-type spring element. When the palm-button 112 is pressed, it moves the cover 110 down toward the base 102, thereby collapsing the extended cover return posts 118 and compressing the return springs 120. When the palm-button 112 is released, the collapsed cover return posts 118 extend and move the cover and palm-button 112 back to the undepressed position via the compressed return springs 120 which expand and extend the cover return posts 118 back to the uncollapsed position.

Figure 4:
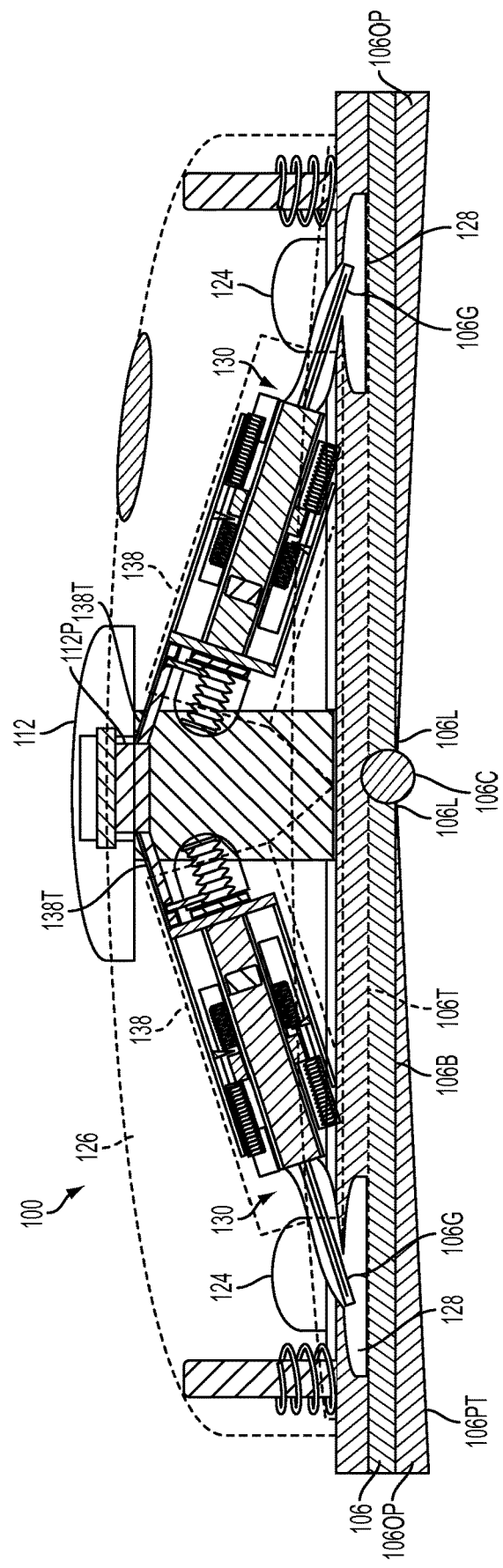
FIG. 4 is another sectional side view of the AI device of FIG. 1.

FIG. 4 is another sectional side view of the AI device 100. As shown therein, the AI device 100 may further comprise one or more injection unit (IU) assemblies 130 operatively connected to a portion 112P of the palm-button 112 that communicates with the interior 126 of the device 100. The multiple IU assemblies 130 are possible because the base 102 of the AI device 100 has a substantially larger mounting surface than conventional "pen-style" autoinjectors. The one or more IU assemblies 130 are positioned within the AI device 100 so that their longitudinal axes may be at an acute angle relative to the base 102, rather than perpendicular to the base 102 as in conventional "pen-style" autoinjectors, to lower the profile of the AI device 100 and increase the stability and ease of use of the device 100. Each IU assembly 130 is operatively associated with an injection chamber 128 provided by a corresponding injection site isolator 124. The IU assemblies 130 and palm-button 112 can be constructed and adapted to provide synchronous and/or asynchronous activation of the IU assemblies 130. Embodiments of the AI device 100 with multiple IU assemblies 130 provide single and/or multiple injection chamber 128 options (e.g. two, three or four injection chambers 128) that allow for larger, combined fluid deliveries, and/or different fluid deliveries, and provide variable injection chambers 128 and locations and configurations to accommodate and adjust drug volumes and avoid injection site reactions. The use of multiple injection chambers 128 can provide active anchoring of the AI device 100 through the configuration of the injection site needle insertion.

FIG. 5 is an enlarged sectional side view of one of the IU assemblies 130 shown in FIG. 4. Each of the IU assemblies 130 may optionally include a heating element 132, a syringe carrier 134, a syringe 136, a carrier drive 138, a plunger drive 140, and a needle guide 142. Each of the IU assemblies 130 may be secured to the base 102 by a support structure 150 formed on or attached to a top surface 102T of the base 102.

Still referring to FIG. 5, the syringe carrier 134 may be constructed and adapted to receive and securely hold the syringe 136 to facilitate needle insertion, drug extrusion, and needle retraction. In some embodiments where the AI device 100 is reusable, the syringe carrier 134 may be constructed and adapted to allow the syringe 136 to be removed after an injection cycle of the AI device 100 and replaced with a new syringe. The syringe carrier 134 may be mounted on, in, or to the support structure 150 so that it is capable of moving in a linear manner relative to the support structure 150 (and the base 102), from a needle retracted position (as shown in FIG. 5), to a needle inserted position (not shown), and then back to the needle retracted position, during an injection cycle of the AI 100. In the shown embodiment, the carrier 134 includes drive abutment tabs 134T. The carrier drive 138 uses the drive abutment tabs 134T to move the carrier 134 from the needle retracted position to the needle inserted position and back to the needle retracted position.

Referring still to FIG. 5, the syringe 136 may conventionally comprise a generally tubular container or barrel 136B, a hypodermic needle 136N or any other element capable of penetrating the user's skin and dispensing a pharmaceutical product or drug into the user, removably or permanently secured to or connected by another conduit to a forward end 136BF of the barrel 136B, a stopper 136S slidably disposed within the barrel 136B, and a plunger rod 136P having a forward end (not visible) operatively engaged with or connected to the stopper 136S and a rearward end 136PR extending out from the barrel 136B at an open rearward end 136BR thereof. A removable, generally tubular needle shield 136NS may be disposed over the needle 136N. The syringe 136 may be filled for treatment or be prefilled with a single dose of a pharmaceutical product or drug. Any other suitable primary container and piercing element arrangement, such as cartridges, ampoules and the like, may be used in place of the syringe 136 in other embodiments of the AI device 100 to penetrate a user's skin and dispense a pharmaceutical product or drug into the user.

Referring still to FIG. 5, the heating element 132, if included in the device, may contact at least a portion of the primary container 136 and is provided for heating the drug contained within the container 136 prior to injection. In some embodiments, the heating element 132 may comprise a sodium acetate-based exothermic heating element. Such a heating element may comprise a trigger-activated sodium acetate bag having a trigger member in the flexible bag for activating the sodium acetate solution. In some embodiments, the heating element 132 can be constructed to be activated by pressing the palm-button 112 such that initial downward movement of the palm-button 112 activates the heating element 132.

In some embodiments of the AI device 100, only one of the IU assemblies 130 may be carrying a syringe 136 with a dose of a pharmaceutical product. The number of the IU assemblies 130 carrying a syringe 136 with a dose of a pharmaceutical depends upon the user's therapy. In various embodiments, the number of IU assemblies can be from one to four, although embodiments with more than four IU assemblies are contemplated, depending upon the user's therapy. In addition, the type of pharmaceutical product and/or the volume of the dose contained in the IU assemblies 130 can be the substantially the same or vary from one IU assembly 130 to another, depending upon the desired treatment.

Figure 6:
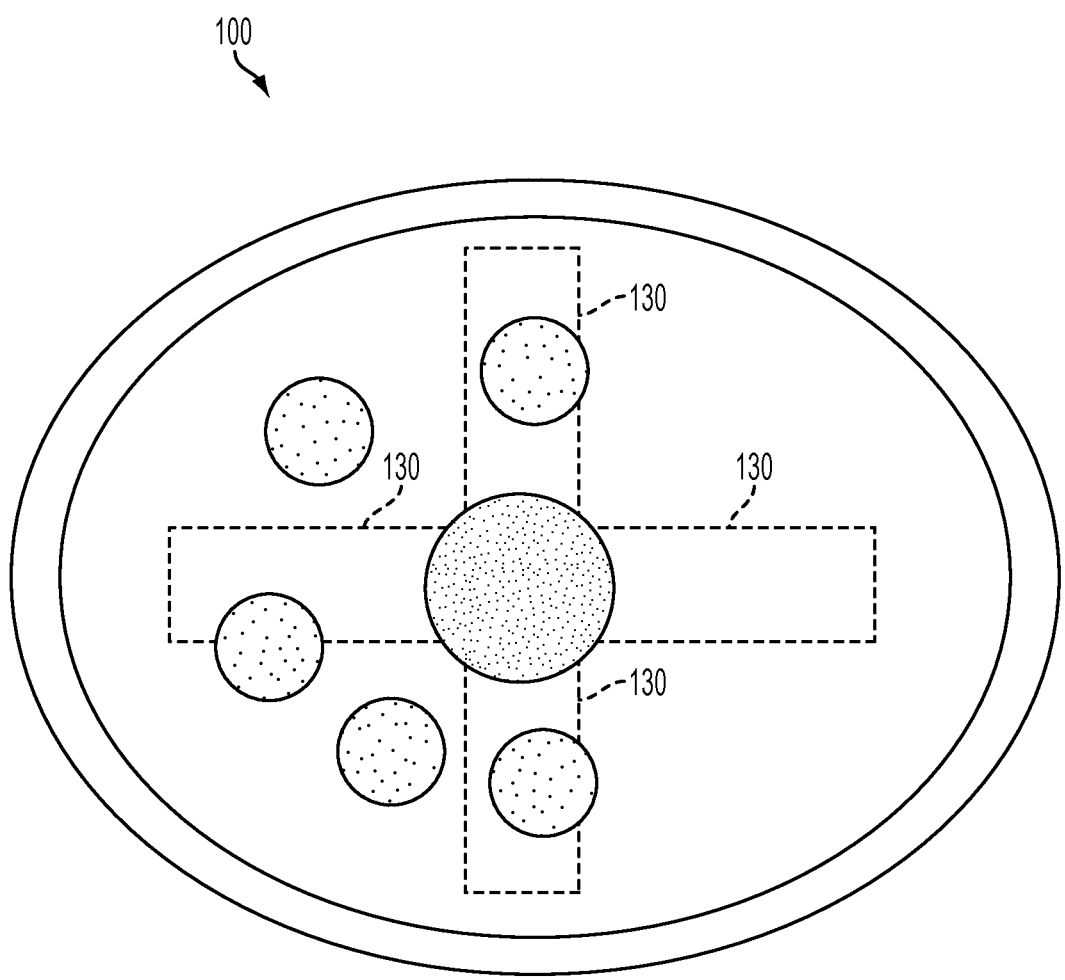
FIG. 6 is a sectional top view of an embodiment of an AI device having four (4) injection unit assemblies.

FIG. 6 is a sectional top view of the AI device 100 having four (4) IU assemblies 130. As shown therein, the IU assemblies 130 may be arranged so that their longitudinal axes are at right angles to one another.

Figure 7:
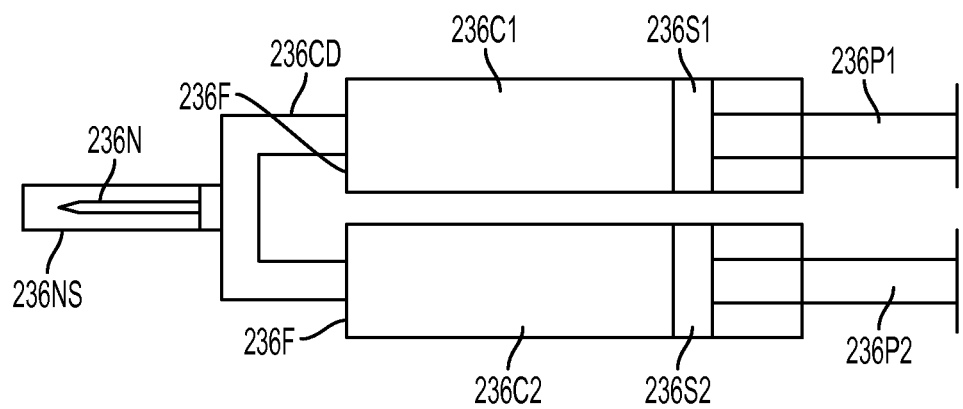
FIG. 7 is a top view of another embodiment of a drug container of the AI device.

As shown in FIG. 7, other embodiments of the AI device may have IU assemblies that each includes two or more containers 236C1, 236C2 instead of a syringe. The containers 236C1, 236C2 may coextend relative to one another. The forward end 236F of each of the containers 236 may be connected to a common hypodermic needle 236N via a bridge conduit 236CD. Each container 236C1, 236C2 may include a stopper 236S1, 236S2 and a plunger rod 236P1, 236P2. A removable, generally tubular needle shield 236NS may be disposed over the needle 236N or other piercing element. The containers 236C1, 236C2 may each be filled for treatment or be prefilled with a single dose of a pharmaceutical product or drug. Alternatively, the containers 236C1 and 236C2 can be each filled for treatment or be prefilled with a different drug. The type of pharmaceutical product and/or the volume of the dose contained in the containers 236C1, 236C2 can be the substantially the same or vary from one container to another, depending upon the desired treatment.

Referring again to FIG. 5, the carrier drive 138 may use the drive tabs 134T of the syringe carrier 134 to move the carrier 134 containing the syringe 136 from the needle retracted position, where the needle 136N is concealed, to the needle inserted position during a needle insertion process of the AI device injection cycle, thereby causing the needle 136N to extend out from the AI device 100, into the injection chamber 128, and penetrate the user's skin drawn into the injection chamber 128. The carrier drive 138 may also use the drive tabs 134T of the syringe carrier 134 to move the carrier 134 containing the syringe 136 back to the needle retracted position from the needle inserted position, thereby withdrawing the needle 136N from the user's skin drawn into the injection chamber 128 and concealing it within the AI device 100. As shown in FIG. 5, some embodiments of the carrier drive 138 may include hollow spring-holding rails 138R, insertion springs 138IS, retraction springs 138RS, carrier trigger rails 138TR, a carrier trigger rail connector 138RC, insertion spring holds 138SH, retraction spring holds 138RH, and a pivoting carrier trigger 138T.

Still referring to FIG. 5, the spring-holding rails 138R may extend generally parallel to the syringe carrier 134 along an outer surface thereof. The rearward ends of the spring-holding rails 138R may be connected to opposing ends of the carrier trigger rail connector 138RC. The carrier trigger rail connector 138RC, in turn, may be connected to the carrier trigger 138T. The carrier trigger 138T may operatively connect the carrier drive 138 to the portion 112P of the palm-button 112 that extends through the cover 110 into the interior 126 of the AI device 100 (FIG. 4). The insertion springs 138 IS and refraction springs 138RS may be contained within the hollow spring-holding rails 138R with each insertion spring 138IS disposed behind a rear abutment surface 134TR of its corresponding drive tab 134T and each retraction spring 138 RS may be engaged with a front abutment surface 134RF of its corresponding drive tab 134T. The insertion spring holds 138SH may be selectively positioned on the carrier trigger rails 138 TR to engage and compress the insertion springs 138IS prior to the commencement of an injection cycle of the AI injection, thereby holding the syringe carrier 134 in the needled retracted position. When the palm-button 112 and cover 110 are pressed down toward the base 102 to activate an injection cycle of the AI device 100, the carrier trigger 138T may pivot and cause the carrier trigger rails 138R to disengage the insertion spring holds 138 SH from the compressed insertion springs 138IS. Once disengaged, the insertion springs 138IS may expand and engage the rear abutment surfaces 134TR of the syringe carrier drive tabs 134T and move the syringe carrier 134 from the needle retracted position to the needle inserted position. As the syringe carrier 134 moves to the needle inserted position, the retraction springs 138RS, which are generally uncompressed, may engage the front abutment surfaces 134TF of the carrier drive tabs 134T (in the needle retracted position), and compress via the spring forces exerted on rear abutment surfaces 134TR of the tabs 134 by the expanding insertion springs 138IS. The insertion springs 138IS may have a higher spring rate than the retraction springs 138RS so that they can compress the retraction springs 138RS and move the syringe carrier 134 to the needle inserted position.

The retraction spring holds 138RH may be selectively positioned on the carrier trigger rails 138TR so that as the palm-button 112 and cover 110 are pressed further down toward the base 102 and the syringe carrier 134 reaches the needle inserted position, the pivoting carrier trigger 138T causes the carrier trigger rails 138TR to engage the retraction spring holds 138RH with the compressed refraction springs 138 RS to hold them in the compressed state until the plunger drive 140 completes drug extrusion. Once drug extrusion is completed and as the palm-button 112 and cover 110 are pressed completely down toward the base 102, the pivoting carrier trigger 138T may cause the carrier trigger rails 138R to disengage the retraction spring holds 138RH from the compressed retraction springs 138RS. Once disengaged, the retraction springs 138RS may expand and engage the front abutment surfaces 134TR of the syringe carrier drive tabs 134T and move the syringe carrier 134 from the needle inserted position back to the needle retracted position.

Referring still to FIG. 5, the plunger drive 140 may push the plunger rod 136P and the stopper 136S, which is operatively connected to the forward end of the plunger rod 136P, down through the syringe barrel 136B to extrude the drug contained within the barrel 136B through the needle 136N and into the user during the drug extrusion process of the AI injection cycle. As shown, some embodiments of the plunger drive 140 may include a pivoting plunger trigger 140T, a plunger hold 140H, and a plunger drive spring 140S. The plunger hold 140 H has one end operatively connected to the plunger trigger 140T and the other end engaged with the plunger rod 136P. The plunger drive spring 140 may be operatively connected to the plunger rod 136P so that in the initial needle retracted position, it is held in a compressed state. When the palm-button 112/cover 110 are pressed down toward the base 102 to activate an injection cycle of the AI device 100, the plunger trigger 140T (as well as the carrier trigger 138T) starts to pivot. When the syringe carrier 134 reaches the needle inserted position which causes the needle 136N to penetrate the user's skin, the pivoting plunger trigger 140T causes the plunger hold 140H to release the plunger rod 136P. Once released, the compressed plunger drive spring 140S expands and pushes the plunger rod 136P and the stopper 136S down through the syringe barrel 136B, thereby extruding the drug contained within the barrel 136B through the needle 136N into the user.

Referring again to FIG. 4, in one embodiment the releasable substrate 106 which covers the flexible layer 104 of the base 102 may be constructed as a need shield remover by providing barb-style or like gripping elements or projections 106G that extend up from the top surface 106T of the substrate 106, into the injection chambers 128 and grip the needle shields 136NS (FIG. 5). When the user is ready to use the AI device 100, he or she simply peels the releasable substrate 106 off the flexible layer 104 to remove all the needle shields 136NS covering the needles 136 N at essentially the same time. To facilitate removal of the releasable substrate 106, a pull tab structure 106PT may be attached to the bottom surface 106B of the substrate 106. The pull tab structure 106PT may include opposing portions 106OP that each has a thickness that gradually increases moving from a center 106C of the pull tab structure 106 PT. The pull tab structure 106PT may also be provided with two parallel lines of weakness 106L located adjacent the center 106C thereof that allow the two thick outer opposing portions 106OP of the pull tab structure 106PT to be folded together to form a pull tab (not shown) which can be easily gripped and pulled with the fingers to remove the peelable substrate 106 from the flexible layer 104 of the base 102.

Other embodiments of the AI device may have various other types of carrier and/or plunger drive mechanisms. Some of these mechanisms may utilize stored energy in any known form including, without limitation, electrical, gas pressure, gas releasing, or any combination thereof. The stored energy can be transmitted by corresponding conventional transmission mechanisms, e.g. electromechanical, such as electric motors or solenoids, hydraulic, pneumatic, gears, rods, and the like. The drive control and activation unit may be provided for activating and sequencing the drive mechanisms and may comprise any well know type of a releasable lock arrangements, electronic controllers, combinations thereof, and the like.

The syringe(s) or other primary container(s) of the AI device may be filled for treatment or be prefilled with a pharmaceutical product, such as an erythropoiesis stimulating agent (ESA), which may be in a liquid or a lyophilized form. An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins comprise erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins comprise, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (comprising EMP1/Hematide), and mimetic antibodies. Exemplary erythropoiesis stimulating proteins comprise erythropoietin, darbepoetin, erythropoietin agonist variants, and peptides or antibodies that bind and activate erythropoietin receptor.

The term erythropoiesis stimulating protein comprises without limitation Epogen® (epoetin alfa), Aranesp® (darbepoetin alfa), Dynepo® (epoetin delta), Mircera® (methyoxy polyethylene glycol-epoetin beta), Hematide™ (peginesatide), MRK-2578, INS-22, Retacrit® (epoetin zeta), Neorecormon® (epoetin beta), Silapo™ (epoetin zeta), Binocrit® (epoetin alfa), epoetin alfa Hexal, Abseamed™ (epoetin alfa), Ratioepo™ (epoetin theta), Eporatio™ (epoetin theta), Biopoin™ (epoetin theta), epoetin alfa, epoetin beta, epoetin zeta, epoetin theta, and epoetin delta.

The term erythropoiesis stimulating protein further comprises the molecules or variants or analogs as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,830,851; 5,856,298; 5,955,422; 5,986,047; 6,030,086; 6,310,078; 6,391,633; 6,583,272; 6,586,398; 6,900,292; 6,750,369; 7,030,226; 7,084,245; and 7,271,689; U.S. Publ. Nos. 2002/0155998; 2003/0077753; 2003/0082749; 2003/0143202; 2003/0215444; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0040858; 2006/0088906; and 2006/0111279; and PCT Publ. Nos. WO 91/05867; WO 95/05465; WO 96/40772; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; WO 2006/29094; and WO 2007/136752.

Alternatively, the syringe(s) or other primary container(s) of the AI device may also be filled for treatment or be prefilled with other products. Examples of other pharmaceutical products that may be used may comprise, but are not limited to, therapeutics such as a biological (e.g., Enbrel® (etanercept, TNF-receptor/Fc fusion protein, TNF blocker), anti-TNF antibodies such as adalimumab, infliximab, certolizumab pegol, and golimumab; anti-IL-12 antibodies such as ustekinumab, other Fc fusions such as CTL4A:Fc also known as abacept; Neulasta® (pegylated filgastrim, pegylated G-CSF, pegylated hu-met-G-CSF), Neupogen® (filgrastim, G-CSF, hu-met-G-CSF), Nplate® (romiplostim), Vectibix® (panitumumab), Sensipar® (cinacalcet), and Xgeva® and Prolia® (each denosamab, AMG 162); as well as other small molecule drugs, a therapeutic antibodies, a polypeptides, proteins or other chemicals, such as an iron (e.g., ferumoxytol, iron dextrans, ferric glyconate, and iron sucrose). The therapeutic may be in liquid form, or reconstituted from lyophilized form.

Among particular illustrative proteins that can be used in the syringe(s) or other primary container(s) of the AI device are antibodies, peptibodies, pegylated proteins, polypeptides, and related proteins (comprising fusions, fragments, analogs, variants or derivatives thereof) for example, proteins that specifically bind to: OPGL; IL-4 receptor; interleukin 1-receptor 1 ("IL1-R1"); angiopoietin-2 (Ang2); NGF; CD22; IGF-1; B-7 related protein 1 (B7RP1); IL-15; IL-17 Receptor A: IFN gamma; TALL-1; parathyroid hormone ("PTH"); thrombopoietin receptor ("TPO-R"); hepatocyte growth factor ("HGF"); TRAIL-R2; Activin A; TGF-beta; amyloid-beta; c-Kit; α4β7: and IL-23 or one of its subunits; and other therapeutic proteins.

The syringe(s) or other primary container(s) of the AI device may also be filled for treatment or be prefilled with OPGL specific antibodies, peptibodies, and related proteins, and the like (also referred to as RANKL specific antibodies, peptibodies and the like), comprising fully humanized and human OPGL specific antibodies, particularly fully humanized monoclonal antibodies, comprising but not limited to the antibodies described in PCT Publ. No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, comprising the OPGL specific antibodies having either the light chain of SEQ ID NO: 2 therein as set forth in FIG. 2 therein and/or the heavy chain of SEQ ID NO:4 therein, as set forth in FIG. 4 therein, each of which is individually and specifically incorporated by reference herein in its entirety fully as disclosed in the foregoing Publication.

The syringe(s) or other primary container(s) of the AI device may also be filled for treatment or be prefilled with myostatin binding proteins, peptibodies, and related proteins, and the like, comprising myostatin specific peptibodies, particularly those described in US Publ. No. 2004/0181033 and PCT Publ. No. WO 2004/058988, which are incorporated by reference herein in their entirety particularly in parts pertinent to myostatin specific peptibodies, comprising but not limited to peptibodies of the mTN8-19 family, comprising those of SEQ ID NOS: 305-351, comprising TN8-19-1 through TN8-19-40, TN8-19 con1 and TN8-19 con2; peptibodies of the mL2 family of SEQ ID NOS: 357-383 therein; the mL15 family of SEQ ID NOS: 384-409; the mL17 family of SEQ ID NOS: 410-438 therein; the mL20 family of SEQ ID NOS: 439-446 therein; the mL21 family of SEQ ID NOS: 447-452 therein; the mL24 family of SEQ ID NOS: 453-454 therein; and those of SEQ ID NOS: 615-631 therein, each of which is individually and specifically incorporated by reference herein in their entirety fully as disclosed in the foregoing publication.

The syringe(s) or other primary container(s) of the AI device may also be filled for treatment or be prefilled with IL-4 receptor specific antibodies, peptibodies, and related proteins, and the like, particularly those that inhibit activities mediated by binding of IL-4 and/or IL-13 to the receptor, comprising those described in PCT Publ. No. WO 2005/047331 or PCT Appl. No. PCT/US2004/03742 and in US Publ. No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication.

The syringe(s) or other primary container(s) of the AI device may also be filled for treatment or be prefilled with IL1-R1 specific antibodies, peptibodies, and related proteins, and the like, comprising but not limited to those described in U.S. Publ. No. 2004/097712A1, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. publication.

The syringe(s) or other primary container(s) of the AI device may also be filled for treatment or be prefilled with Ang2 specific antibodies, peptibodies, and related proteins, and the like, comprising but not limited to those described in PCT Publ. No. WO 03/057134 and U.S. Publ No. 2003/0229023, each of which is incorporated herein by reference in its entirety particularly in parts pertinent to Ang2 specific antibodies and peptibodies and the like, especially those of sequences described therein and comprising but not limited to: L1 (N); L1 (N) WT; L1 (N) 1K WT; 2×L1 (N); 2×L1 (N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8 (N); TN8-14 (N); Con 1 (N), also comprising anti-Ang 2 antibodies and formulations such as those described in PCT Publ. No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication.

The syringe(s) or other primary container(s) of the AI device may also be filled for treatment or be prefilled with NGF specific antibodies, peptibodies, and related proteins, and the like comprising, in particular, but not limited to those described in US Publ. No. 2005/0074821 and U.S. Pat. No. 6,919,426, which are incorporated herein by reference in their entirety particularly as to NGF-specific antibodies and related proteins in this regard, comprising in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication.

The syringe(s) or other primary container(s) of the AI device may also be filled for treatment or be prefilled with CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, comprising but not limited to humanized and fully human monoclonal antibodies, particularly comprising but not limited to human CD22 specific IgG antibodies, such as, for instance, a dimer of a human-mouse monoclonal hLL2 gamma-chain disulfide linked to a human-mouse monoclonal hLL2 kappa-chain, comprising, but limited to, for example, the human CD22 specific fully humanized antibody in Epratuzumab, CAS registry number 501423-23-0;

The syringe(s) or other primary container(s) of the AI device may also be filled for treatment or be prefilled with IGF-1 receptor specific antibodies, peptibodies, and related proteins, and the like, such as those described in PCT Publ. No. WO 06/069202, which is incorporated herein by reference in its entirety as to IGF-1 receptor specific antibodies and related proteins, comprising but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing International Publication.

Also among non-limiting examples of anti-IGF-1R antibodies for use in the methods and compositions of the disclosure are each and all of those described in: (i) US Publ. No. 2006/0040358 (published Feb. 23, 2006), 2005/0008642 (published Jan. 13, 2005), 2004/0228859 (published Nov. 18, 2004), comprising but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein; (ii) PCT Publ. No. WO 06/138729 (published Dec. 28, 2006) and WO 05/016970 (published Feb. 24, 2005), and Lu et al., 2004, J Biol. Chem. 279:2856-65, comprising but not limited to antibodies 2F8, A12, and IMC-A12 as described therein; (iii) PCT Publ. No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003); (iv) US Publ. No. 2005/0084906 (published Apr. 21, 2005), comprising but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein; (v) US Publ. Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al., 2003, Cancer Res. 63:5073-83, comprising but not limited to antibody EM164, resurfaced EM164, humanized EM164, huEM164 v1.0, huEM164 v1.1, huEM164 v1.2, and huEM164 v1.3 as described therein; (vi) U.S. Pat. No. 7,037,498 (issued May 2, 2006), US Publ. Nos. 2005/0244408 (published Nov. 30, 2005) and 2004/0086503 (published May 6, 2004), and Cohen, et al., 2005, Clinical Cancer Res. 11:2063-73, e.g., antibody CP-751,871, comprising but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein; (vii) US Publ. Nos. 2005/0136063 (published Jun. 23, 2005) and 2004/0018191 (published Jan. 29, 2004), comprising but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) US Publ. No. 2004/0202655 (published Oct. 14, 2004), comprising but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors.

The syringe(s) or other primary container(s) of the AI device may also be filled for treatment or be prefilled with B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publ. No. 2008/0166352 and PCT Publ. No. WO 07/011941, which are incorporated herein by reference in their entireties as to such antibodies and related proteins, comprising but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing U.S. Publication.

The syringe(s) or other primary container(s) of the AI device may also be filled for treatment or be prefilled with IL-15 specific antibodies, peptibodies, and related proteins, and the like, such as, in particular, humanized monoclonal antibodies, particularly antibodies such as those disclosed in U.S. Publ. Nos. 2003/0138421; 2003/023586; and 2004/0071702; and U.S. Pat. No. 7,153,507, each of which is incorporated herein by reference in its entirety as to IL-15 specific antibodies and related proteins, comprising peptibodies, comprising particularly, for instance, but not limited to, HuMax IL-15 antibodies and related proteins, such as, for instance, 146B7.

The syringe(s) or other primary container(s) of the AI device may also be filled for treatment or be prefilled with pharmaceutical compositions comprising antagonistic human monoclonal antibodies against human IL-17 Receptor A. The characterization, cloning, and preparation of IL-17 Receptor A are described in U.S. Pat. No. 6,072,033, issued Jun. 6, 2000, which is incorporated herein by reference in its entirety. The amino acid sequence of the human IL-17RA is shown in SEQ ID NO:10 of U.S. Pat. No. 6,072,033 (GenBank accession number NM_014339). Such antibodies may comprise those disclosed in WO 2008/054603, which is incorporated by reference in its entirety or the antibodies claimed in U.S. Pat. No. 7,767,206, issued Aug. 3, 2010, and in U.S. Ser. No. 11/906,094, which are incorporated by reference in their entirety.

The syringe(s) or other primary container(s) of the AI device may also be filled for treatment or be prefilled with IFN gamma specific antibodies, peptibodies, and related proteins and the like, especially human IFN gamma specific antibodies, particularly fully human anti-IFN gamma antibodies, such as, for instance, those described in US Publ. No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing US Publication and in Thakur et al., Mol. Immunol. 36:1107-1115 (1999). In addition, description of the properties of these antibodies provided in the foregoing US publication is also incorporated by reference herein in its entirety. Specific antibodies comprise those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing US Publication. A specific antibody contemplated is antibody 1119 as disclosed in foregoing US Publication and having a complete heavy chain of SEQ ID NO:17 as disclosed therein and having a complete light chain of SEQ ID NO:18 as disclosed therein.

The syringe(s) or other primary container(s) of the AI device may also be filled for treatment or be prefilled with TALL-1 specific antibodies, peptibodies, and related proteins, and the like, and other TALL specific binding proteins, such as those described in U.S. Publ. Nos. 2003/0195156 and 2006/0135431, each of which is incorporated herein by reference in its entirety as to TALL-1 binding proteins, particularly the molecules of Tables 4 and 5B therein, each of which is individually and specifically incorporated by reference herein in its entirety fully as disclosed in the foregoing US Publications.

The syringe(s) or other primary container(s) of the AI device may also be filled for treatment or be prefilled with PTH specific antibodies, peptibodies, and related proteins, and the like, such as those described in U.S. Pat. No. 6,756,480, which is incorporated herein by reference in its entirety, particularly in parts pertinent to proteins that bind PTH.

The syringe(s) or other primary container(s) of the AI device may also be filled for treatment or be prefilled with TPO-R specific antibodies, peptibodies, and related proteins, and the like, such as those described in U.S. Pat. No. 6,835,809, which is herein incorporated by reference in its entirety, particularly in parts pertinent to proteins that bind TPO-R.

The syringe(s) or other primary container(s) of the AI device may also be filled for treatment or be prefilled with HGF specific antibodies, peptibodies, and related proteins, and the like, comprising those that target the HGF/SF:cMet axis (HGF/SF:c-Met), such as the fully human monoclonal antibodies that neutralize hepatocyte growth factor/scatter (HGF/SF) described in US Publ. No. 2005/0118643 and PCT Publ. No. WO 2005/017107, huL2G7 described in U.S. Pat. No. 7,220,410 and OA-5d5 described in U.S. Pat. Nos. 5,686,292 and 6,468,529 and in PCT Publ. No. WO 96/38557, each of which is incorporated herein by reference in its entirety, particularly in parts pertinent to proteins that bind HGF.

The syringe(s) or other primary container(s) of the AI device may also be filled for treatment or be prefilled with TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2.

The syringe(s) or other primary container(s) of the AI device may also be filled for treatment or be prefilled with Activin A specific antibodies, peptibodies, related proteins, and the like, comprising but not limited to those described in US Publ. No. 2009/0234106, which is herein incorporated by reference in its entirety, particularly in parts pertinent to proteins that bind Activin A.

The syringe(s) or other primary container(s) of the AI device may also be filled for treatment or be prefilled with TGF-beta specific antibodies, peptibodies, related proteins, and the like, comprising but not limited to those described in U.S. Pat. No. 6,803,453 and US Publ. No. 2007/0110747, each of which is herein incorporated by reference in its entirety, particularly in parts pertinent to proteins that bind TGF-beta.

The syringe(s) or other primary container(s) of the AI device may also be filled for treatment or be prefilled with amyloid-beta protein specific antibodies, peptibodies, related proteins, and the like, comprising but not limited to those described in PCT Publ. No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in the International Publication.

The syringe(s) or other primary container(s) of the AI device may also be filled for treatment or be prefilled with c-Kit specific antibodies, peptibodies, related proteins, and the like, comprising but not limited to those described in Publ. No. 2007/0253951, which is incorporated herein by reference in its entirety, particularly in parts pertinent to proteins that bind c-Kit and/or other stem cell factor receptors.

The syringe(s) or other primary container(s) of the AI device may also be filled for treatment or be prefilled with OX40L specific antibodies, peptibodies, related proteins, and the like, comprising but not limited to those described in U.S. application Ser. No. 11/068,289, which is incorporated herein by reference in its entirety, particularly in parts pertinent to proteins that bind OX40L and/or other ligands of the OXO40 receptor.

The syringe(s) or other primary container(s) of the AI device may also be filled for treatment or be prefilled with other exemplary proteins comprising but are not limited to Activase® (Alteplase, tPA); Aranesp® (Darbepoetin alfa), Epogen® (Epoetin alfa, or erythropoietin); Avonex® (Interferon beta-1a); Bexxar® (Tositumomab, anti-CD22 monoclonal antibody); Betaseron® (Interferon-beta); Campath® (Alemtuzumab, anti-CD52 monoclonal antibody); Dynepo® (Epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (Epoetin alfa); Erbitux® (Cetuximab, anti-EGFR/HER1/c-ErbB-1); Genotropin® (Somatropin, Human Growth Hormone); Herceptin® (Trastuzumab, anti-HER2/neu (erbB2) receptor mAb); Humatrope® (Somatropin, Human Growth Hormone); Humira® (Adalimumab); Insulin in Solution; Infergen® (Interferon Alfacon-1); Natrecor® (nesiritide; recombinant human B-type natriuretic peptide (hBNP); Kineret® (Anakinra), Leukine® (Sargamostim, rhuGM-CSF); LymphoCide® (Epratuzumab, anti-CD22 mAb); Lymphostat B® (Belimumab, anti-BlyS mAb); Metalyse® (Tenecteplase, t-PA analog); Mircera® (methoxy polyethylene glycol-epoetin beta); Mylotarg® (Gemtuzumab ozogamicin); Raptiva® (efalizumab); Cimzia® (certolizumab pegol, CDP 870); Soliris™ (Eculizumab); Pexelizumab (Anti-C5 Complement); MEDI-524 (Numax®); Lucentis® (Ranibizumab); 17-1A (Edrecolomab, Panorex®); Trabio® (lerdelimumab); TheraCim hR3 (Nimotuzumab); Omnitarg (Pertuzumab, 2C4); Osidem® (IDM-1); OvaRex® (B43.13); Nuvion® (visilizumab); Cantuzumab mertansine (huC242-DM1); NeoRecormon® (Epoetin beta); Neumega® (Oprelvekin, Human Interleukin-11); Neulasta® (Pegylated filgastrim, pegylated G-CSF, pegylated hu-Met-G-CSF); Neupogen® (Filgrastim, G-CSF, hu-MetG-CSF); Orthoclone OKT3® (Muromonab-CD3, anti-CD3 monoclonal antibody), Procrit® (Epoetin alfa); Remicade® (Infliximab, anti-TNFα monoclonal antibody), Reopro® (Abciximab, anti-GP 1Ib/IIia receptor monoclonal antibody), Actemra® (anti-IL6 Receptor mAb), Avastin® (Bevacizumab), HuMax-CD4 (zanolimumab), Rituxan® (Rituximab, anti-CD20 mAb); Tarceva® (Erlotinib); Roferon-A®-(Interferon alfa-2a); Simulect® (Basiliximab); Prexige® (lumiracoxib); Synagis® (Palivizumab); 146B7-CHO (anti-IL15 antibody, see U.S. Pat. No. 7,153,507), Tysabri® (Natalizumab, anti-α4integrin mAb); Valortim® (MDX-1303, anti-B. anthracis Protective Antigen mAb); ABthrax™; Vectibix® (Panitumumab); Xolair® (Omalizumab), ETI211 (anti-MRSA mAb), IL-1 Trap (the Fc portion of human IgG1 and the extracellular domains of both IL-1 receptor components (the Type I receptor and receptor accessory protein)), VEGF Trap (Ig domains of VEGFR1 fused to IgG1 Fc), Zenapax® (Daclizumab); Zenapax® (Daclizumab, anti-IL-2Rα mAb), Zevalin® (Ibritumomab tiuxetan), Zetia (ezetimibe), Atacicept (TACI-Ig), anti-CD80 monoclonal antibody (mAb) (galiximab), anti-CD23 mAb (lumiliximab). BR2-Fc (huBR3/huFc fusion protein, soluble BAFF antagonist); CNTO 148 (Golimumab, anti-TNFα mAb); HGS-ETR1 (Mapatumumab; human anti-TRAIL Receptor-1 mAb); HuMax-CD20 (Ocrelizumab, anti-CD20 human mAb); HuMax-EGFR (zalutumumab); M200 (Volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Rα mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2; a sclerostin antibody, such as but not limited to romosozumab, blosozumab, or BPS 804 (Novartis). Also included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the AI can be a monoclonal antibody (IgG) that binds human Proprotein Convertase Subtilisin/Kexin Type 9 (PCSK9), e.g. U.S. Pat. No. 8,030,547, U.S. Ser. No. 13/469,032, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

The syringe(s) or other primary container(s) of the AI device may also be filled for treatment or be prefilled with antibodies comprising, but not limited to, those that recognize any one or a combination of proteins comprising, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEGF receptor, hepatocyte growth factor, osteoprotegerin ligand, interferon gamma, B lymphocyte stimulator (BlyS), also known as BAFF, THANK, TALL-1, and zTNF4; see Do and Chen-Kiang (2002), Cytokine Growth Factor Rev. 13(1): 19-25), C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (Ep-CAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, Respiratory Syncitial Virus, human immunodeficiency virus (HIV), hepatitis B virus (HBV), *Streptococcus mutans*, and *Staphlycoccus aureus*.

Additional examples of known antibodies that may be contained in the syringe(s) or other primary container(s) of the AI device can comprise but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, zalutumumab, and zanolimumab.

It should be understood that the configuration is not limited to being dome-shaped and any shape that provides an appropriate ergonomic effect can be used, provided that it meets other criteria described herein Although the AI device of the disclosure has been described in terms of illustrative embodiments, it is not limited thereto. Rather, the appended claims should be construed broadly, to comprise other variants and embodiments of the AI device, which may be made by those skilled in the art without departing from the scope and range of equivalents of the AI device and its elements.

What is claimed is:

1. An injector for delivering a therapeutic product comprising:
    a base having a bottom surface;
    a flexible layer coupled to the bottom surface of the base that conforms to various body contours of a patient;
    an injection chamber, wherein the flexible layer forms a vacuum with the skin of the patient and the vacuum draws the skin of the patient into the injection chamber;
    a cover disposed over the base;
    a vent aperture, wherein the cover is movable relative to the base from a first position to a second position to cause air to move through the vent aperture for releasing the vacuum generated between the flexible layer and the skin, the cover and base being coupled together in both the first position and the second position; and
    a flexible isolator disposed over the injection chamber, the isolator having a concave surface for drawing a portion of the skin up into the injection chamber.

2. The injector of claim 1, further comprising:
    a container or syringe disposed within the injector, the container or syringe containing a therapeutic product;
    a needle shield removably attached to the container or syringe; and
    a peelable substrate disposed over the flexible layer for removing the needle shield from the container or syringe.

3. The injector of claim 2, wherein the peelable substrate comprises:
    a structure which can be folded into a pull-tab to facilitate removal of the peelable substrate from the flexible layer; or
    a structure with opposing portions that can be folded down against one another to facilitate removal of the peelable substrate from the flexible layer; or
    a projection extending from an attachment surface thereof for attaching the peelable substrate to the needle shield.

4. The injector of claim 2, wherein the cover has a window for viewing the container or syringe during an injection cycle of the injector.

5. The injector of claim 2, wherein the container or syringe has a needle for injecting the therapeutic product contained within the container or syringe into the patient and further comprising a carrier provided on the base, the carrier for moving the container or syringe between a first position and a second position during an injection cycle of the injector, the needle disposed within the injector in the first position, the needle extending from the base in the second position.

6. The injector of claim 5, wherein the container or syringe has a plunger for dispensing the therapeutic product from the container or syringe and through the needle and further comprising a plunger drive for driving the plunger through the container or syringe to dispense the therapeutic product from the container or syringe and through the needle, the plunger drive comprising a spring, a hydraulic actuator, or any combination thereof, wherein the plunger drive is activated by pressing the cover toward the base.

7. The injector of claim 5, further comprising a carrier drive for moving the carrier between the first position and the second position, the carrier drive having a spring drive element, a hydraulic drive element, or any combination thereof, wherein the carrier drive is activated by pressing the cover toward the base.

8. The injector of claim 7, wherein the carrier drive is disposed at an acute angle relative to the base.

9. The injector of claim 8, further comprising a needle guide for bending the needle into the injection chamber.

10. The injector of claim 5, further comprising a heating element disposed adjacent to the carrier for heating the therapeutic product contained in the container or syringe.

11. The injector of claim 10, wherein the heating element comprises an exothermic heating element.

12. The injector of claim 5, wherein the container or syringe has a plunger for dispensing the therapeutic product from the container or syringe and through the needle and further comprising a plunger drive for driving the plunger through the container or syringe to dispense the therapeutic product from the container or syringe and through the needle and a carrier drive for moving the carrier between the first and second positions, each of the plunger and carrier drives having, a spring drive element, a hydraulic drive element, or any combination thereof, wherein at least one of the plunger and carrier drives is activated by pressing the cover toward the base.

13. The injector of claim 5, wherein the container or syringe comprises at least two barrels coupled to the needle, each barrel containing a therapeutic product.

14. The injector of claim 5, further comprising at least a second carrier.

15. The injector of claim 14, further comprising at least a second container or syringe, the second carrier for moving the second container or syringe between the first position and the second position.

16. The injector of claim 1, wherein the cover comprises at least one of: a palm-button for pressing the cover toward the base to start an injection cycle of the injector, at least one finger-pad for gripping the injector, or a layer of material for hand or finger gripping of the injector.

17. The injector of claim 16, wherein the at least one finger-pad is located on the cover to meet a gripping requirement of a certain patient population.

18. The injector of claim 1, wherein the injector has a low profile with a height less than a width.

19. The injector of claim 1, wherein the flexible layer is further for stretching or pinching the skin.

20. An injector for delivering a therapeutic product comprising:
   a base having a bottom surface;
   a flexible layer coupled to the bottom surface of the base that conforms to various body contours of a patient;
   an injection chamber, wherein the flexible layer forms a vacuum with the skin of the patient and the vacuum draws the skin of the patient into the injection chamber;
   a cover disposed over the base;
   a vent aperture, wherein the cover is movable relative to the base from a first position to a second position to cause air to move through the vent aperture for releasing the vacuum generated between the flexible layer and the skin, the cover and base being coupled together in both the first position and the second position;
   a container or syringe disposed within the injector, the container or syringe containing a therapeutic product;
   a needle shield removably attached to the container or syringe; and
   a peelable substrate disposed over the flexible layer for removing the needle shield from the container or syringe.

* * * * *